United States Patent
Jugl et al.

(10) Patent No.: US 10,092,699 B2
(45) Date of Patent: Oct. 9, 2018

(54) MEDICAL DEVICE PROTECTION ASSEMBLY IN THE FORM OF AN ATTACHABLE WEIGHT ACTING AS IMPACT-ABSORBING STRUCTURE

(71) Applicant: SANOFI-AVENTIS DEUTSCHLAND GMBH, Frankfurt am Main (DE)

(72) Inventors: Michael Jugl, Frankfurt am Main (DE); Axel Teucher, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 14/423,734

(22) PCT Filed: Aug. 28, 2013

(86) PCT No.: PCT/EP2013/067753
§ 371 (c)(1),
(2) Date: Feb. 25, 2015

(87) PCT Pub. No.: WO2014/033143
PCT Pub. Date: Mar. 6, 2014

(65) Prior Publication Data
US 2015/0202370 A1 Jul. 23, 2015

(30) Foreign Application Priority Data
Aug. 31, 2012 (EP) .................... 12182525

(51) Int. Cl.
*A61M 5/24* (2006.01)
*A61M 5/00* (2006.01)
(Continued)

(52) U.S. Cl.
CPC .............. *A61M 5/24* (2013.01); *A61M 5/003* (2013.01); *A61M 5/14244* (2013.01);
(Continued)

(58) Field of Classification Search
CPC .... A61B 2562/18; A61M 2005/14264; A61M 2205/0216
See application file for complete search history.

(56) References Cited

U.S. PATENT DOCUMENTS 7,727,203 B2 * 6/2010 Shimazaki .......... A61M 5/3134
604/240
8,749,958 B2 6/2014 Li
(Continued)

FOREIGN PATENT DOCUMENTS

CN 2525573 Y 12/2002
CN 101244298 A 8/2008
(Continued)

OTHER PUBLICATIONS

International Search Report for Int. App. No. PCT/EP2013/067753, completed Oct. 15, 2013.
(Continued)

*Primary Examiner* — Manuel Mendez
(74) *Attorney, Agent, or Firm* — McCarter & English, LLP

(57) ABSTRACT

The present invention relates to a medical device protection assembly and to a respective medical device. The protection assembly comprises at least one reorientation member being connectable with a medical device and being operable to orient the medical device into a predefined orientation in the event the medical device is subject to a free-fall.

13 Claims, 2 Drawing Sheets

(51) Int. Cl.
    *A61M 5/142* (2006.01)
    *A61B 5/145* (2006.01)
(52) U.S. Cl.
    CPC ....... *A61B 5/14532* (2013.01); *A61B 2562/18* (2013.01); *A61M 2005/14264* (2013.01); *A61M 2205/0216* (2013.01); *A61M 2207/00* (2013.01); *A61M 2230/201* (2013.01)

(56) References Cited

U.S. PATENT DOCUMENTS

| | | | | |
|---|---|---|---|---|
| 8,880,221 | B2* | 11/2014 | Lee | B62D 57/032 318/568.12 |
| 2006/0140798 | A1 | 6/2006 | Kutsuzawa | |
| 2006/0184138 | A1* | 8/2006 | Shimazaki | A61M 5/3134 604/240 |
| 2007/0185450 | A1 | 8/2007 | De Polo et al. | |
| 2008/0183133 | A1* | 7/2008 | Kiersh | A61M 5/14244 604/131 |
| 2012/0123338 | A1* | 5/2012 | Rouleau | A61M 5/14244 604/151 |
| 2012/0245735 | A1* | 9/2012 | Lee | B62D 57/032 700/255 |
| 2013/0073095 | A1* | 3/2013 | King | H04M 1/185 700/279 |
| 2015/0108030 | A1 | 4/2015 | Yin | |
| 2015/0238124 | A1* | 8/2015 | Buckman | A61B 5/1117 600/595 |
| 2015/0351666 | A1* | 12/2015 | Buckman | A61B 5/1117 600/595 |
| 2016/0067422 | A1* | 3/2016 | Davis | A61M 5/3202 604/192 |

FOREIGN PATENT DOCUMENTS

| | | |
|---|---|---|
| CN | 101765346 A | 6/2010 |
| CN | 201557341 U | 8/2010 |
| CN | 201910977 U | 7/2011 |
| CN | 202003685 U | 10/2011 |
| CN | 102638954 A | 8/2012 |
| EP | 1683535 | 7/2006 |
| EP | 1952835 | 8/2008 |
| EP | 1980929 | 10/2008 |
| JP | 2000-232271 A | 8/2000 |
| JP | 2001-057477 A | 2/2001 |
| JP | 2006-066790 A | 3/2006 |
| JP | 2011-005182 A | 1/2011 |
| WO | 2008/077914 | 7/2008 |
| WO | 2011/159930 | 12/2011 |

OTHER PUBLICATIONS

Chinese Office Action for CN Application No. 201380043548.8, dated Oct. 28, 2016.
Chinese Search Report for CN Application No. 201380043548.8, dated Oct. 19, 2016.

* cited by examiner

MEDICAL DEVICE PROTECTION ASSEMBLY IN THE FORM OF AN ATTACHABLE WEIGHT ACTING AS IMPACT-ABSORBING STRUCTURE

CROSS REFERENCE TO RELATED APPLICATIONS

The present application is a U.S. National Phase Application pursuant to 35 U.S.C. § 371 of International Application No. PCT/EP2013/067753 filed Aug. 28, 2013, which claims priority to European Patent Application No. 12182525.1 filed Aug. 31, 2012. The entire disclosure contents of these applications are herewith incorporated by reference into the present application.

TECHNICAL FIELD

The present invention relates to the field of portable medical devices and in particular to a protection assembly adapted to protect medical devices against mechanical impact.

BACKGROUND

There exists a variety of portable medical devices such like injection devices or analysis devices, by way of which a patient may conduct self-treatment, in particular self-administration of a medicament.

Especially with patients suffering diabetes, a blood glucose level has to be regularly determined, e.g. by making use of a blood glucose measurement device (BGM). Depending on the measured data and a determined blood glucose concentration the patient may then individually select a dose of a medicament which is to be administered, e.g. by way of injection.

There exists a large variety of medical devices for analysing and treating patients for diagnostic and/or therapeutic purpose. Such medical devices are sometimes rather fragile and sensitive to mechanical impact.

In general, medical devices may comprise a variety of sensitive components which require sufficient protection against external hazards. Portable or mobile medical devices may also comprise a large variety of electronic components, by way of which various functionalities of the device can be configured, controlled and conducted. Additionally, such devices may comprise various input and/or output means, such like a display, operating buttons and knobs, regulators, dose dials and so on.

Moreover, medical devices may also comprise a storage module by way of which repeated use of the medical device can be monitored and logged. Also, medical devices may comprise a communication module, such like an interface, by way of which treatment-related or device-configuration-related data can be exchanged with additional devices, such like personal computers or smartphones.

The various components of such portable medical devices may be rather susceptible to mechanical impact and may affect the general operability of such devices when exposed to mechanical impact above a certain threshold.

It is therefore an object of the present invention to provide a medical device protection assembly by way of which the susceptibility of the medical device against mechanical impact can be reduced and by way of which the mechanical resistivity of the medical device against mechanical impact or comparable hazards can be improved. It is a particular aim to provide a medical device protection assembly, which is adaptable to existing medical devices and which can be retrofitted. Moreover, the medical device protection assembly should comprise a rather simple and intuitive structure. It should be easy to use and should be highly acceptable by end consumers. Furthermore, it should be manufacturable in a cost-efficient way.

SUMMARY

In a first aspect, a medical device protection assembly is provided which comprises at least one reorientation member being connectable with a medical device to be protected. The at least one reorientation member is operable to orient, hence to turn or to reorient the medical device into a predefined orientation in the event that the medical device is subject to a free-fall. In the event the medical device gets lost or drops down to a ground surface, the reorientation member serves to orient the medical device into a predefined orientation, in which the medical device is less susceptible to mechanical impact.

In other words, the reorientation member is operable to turn the medical device into an orientation in which the medical device per se features a beneficial robustness against mechanical impact. The reorientation member may for instance serve to turn the medical device into an orientation, in which at least a rather sensitive component, such like a display, faces away from the ground surface. This way, such sensitive components can be effectively protected even in the event that the medical device—for which ever reason—drops down to the ground.

The reorientation member is adapted to be directly interconnected with the housing of the medical device. Alternatively, the reorientation member may also be provided as a particular component of the medical device itself, wherein the position and/or configuration of the reorientation member on or inside the housing of the medical device serves to reorient or to turn the medical device into a predefined orientation if the medical device is subject to a free-fall.

This way, the at least one reorientation member is adapted to provide and/or to induce a well-defined falling-down behaviour of the medical device.

In a preferred embodiment, the reorientation member comprises a reorientation weight to modify the device's centre of gravity. The reorientation member may be designed as an attachable weight piece, by way of which the centre of gravity of the medical device can be shifted and displaced towards a particular end section of the housing of the medical device. Then, in the event of a free-fall of the medical device, the device may start to rotate in such a way, that the portion of the housing of the medical device, which is operably connected with the reorientation member hits or impacts a ground surface first.

In embodiments, wherein the medical device comprises a drug delivery or injection device, such like a pen-type injector, the reorientation member may for instance be attached to a proximal portion of the medical device, which faces away from a distal injection end of the device. Then, if the device becomes subject to a free-fall, the device presumably impacts a ground surface with its proximal end, thereby inherently protecting a distal end of the device, where a tipped needle or a breakable container containing a medicament, such like a cartridge, is typically located.

In a further preferred embodiment, the medical device protection assembly comprises an impact receiving structure to cover at least a portion of a housing of the medical device. The impact receiving structure is particularly adapted to hit or to impact a ground surface first in the event of a free-fall of the medical device. Consequently the impact receiving structure may be structurally reinforced or structurally enhanced in order to withstand respective mechanical impact.

By way of the impact receiving structure covering at least a portion of the housing of the medical device, a mechanical impact incident on a particular portion of the impact receiving structure may distribute and dissipate in the impact receiving structure and may be transferred in a well-defined way into adjacent housing portions of the medical device.

In a further embodiment, the impact receiving structure may also at least partially cover the reorientation member. Hence, the impact receiving structure and the reorientation member may be provided as a pre-configured unit which serves as a medical device protection assembly being configured and being operable to be connected to a particular portion of the housing of the medical device.

In other embodiments it is also conceivable that the function of the impact receiving structure is integrated and/or embedded in the reorientation member. Then, the reorientation member not only serves to reorient the medical device in the event of a free-fall but also serves as an impact receiving structure, which by its shape and position is adapted to impact a ground surface first in the event of a free-fall of the medical device. In other words, the reorientation member may provide a kind of crash zone adapted to receive, to absorb and/or to transfer externally applied mechanical impact.

In a further embodiment, the reorientation member is fixable to the housing of the medical device by means of the impact receiving structure. By covering at least a portion of the reorientation member and by covering at least a portion of the housing of the medical device, the impact receiving structure may at the same time provide a fixing arrangement for fixing the reorientation member to the housing of the drug delivery device. Here, the reorientation member does not have to be separately fixed to the medical device. Instead, the reorientation member may be preassembled with the impact receiving structure, which in turn is to be fixed and assembled to the housing of the medical device.

Additionally or alternatively it is also conceivable, that the reorientation member is to be fixed to the housing of the medical device by means of squeezing the reorientation member between the housing of the medical device and the impact receiving structure to be connected thereto.

In an alternative embodiment the impact receiving structure is fixable to the housing of the medical device by means of the reorientation member. Then, the impact receiving structure does not have to be individually connected with the housing. It may then be sufficient, if the impact receiving structure at least partially covers the reorientation member, which itself is releasably or non-releasably connectable to the housing of the medical device.

According to another embodiment, the reorientation member and/or the impact receiving structure comprise or form a receptacle to receive at least a portion of the housing of the medical device. In effect, the reorientation member and/or the impact receiving structure may provide a kind of crash-cap to be mounted on a particular end section of the housing of the medical device. Here, due to its additional weight, the reorientation member may induce a well-defined turning or reorientation of the medical device in the event of a free-fall whereas the impact receiving structure serves to receive, to absorb and/or to transfer mechanical impact to the housing of the medical device in a well defined way.

In particular embodiments, the medical device protection assembly may provide a kind of a crash cap to be mounted on a particular end of the housing of the medical device.

In a further embodiment, the reorientation member and/or the impact receiving structure are releasably engageable with the housing of the medical device. A releasable engagement can be attained by means of a positive interlock or by means of a frictional engagement between the medical device and its medical device protection assembly.

The reorientation member and/or impact receiving structure may for instance be releasably clipped or clamped to the housing of the medical device. A releasable engagement of the medical device protection assembly and the medical device allows to remove and/or to replace a medical device protection assembly in the event it has been damaged.

Instead of a releasable engagement of the medical device protection assembly and the medical device it is also conceivable to non-releasably, hence, to permanently connect the medical device protection assembly and the medical device. Then, in the event the medical device becomes subject to a respective mechanical impact, the end user can be encouraged or even be forced to bring the medical device to a customer service for checking whether the medical device is still intact.

In a further embodiment, the reorientation member is not arranged outside but inside the housing of the medical device. The reorientation member may be fixed to an inside facing portion of the housing or may be fixed to a separate support structure of the device located inside the housing. Here, the reorientation member may be positioned at a particular end section of the housing in order to induce a well-defined turning or reorienting of the medical device in the event of a free-fall.

In a further embodiment, it is of particular benefit, when the internally arranged reorientation member comprises a battery or a comparable energy storage device, which by its nature comprises a comparatively high weight.

In a further aspect, the impact receiving structure is mechanically reinforced. It may comprise a comparatively hard shell, which protects a respective portion of the housing of the medical device, which is at least partially covered by said impact receiving structure. Moreover, by providing a comparatively hard and inelastic impact receiving structure, a mechanical impact being incident at a particular portion of the impact receiving structure may be distributed across the impact receiving structure rather than absorbed. In this way, incident mechanical impact can be transferred across the impact receiving structure and into the housing of the medical device interconnected therewith in a well-defined but comparatively less defective way.

In particular embodiments, the impact receiving structure may comprise a piece of sheet metal or a comparatively hard plastic material, such like thermosetting polymers.

Apart from that it is conceivable that the impact receiving structure comprises an injection molded component, which might be fibre reinforced.

In a further embodiment, the medical device protection assembly also comprises an impact absorbing structure, by way of which kinetic energy and/or momentum of an impact being incident on the impact receiving structure can be at least partially absorbed and/or effectively dissipated. The impact absorbing structure preferably comprises a rather soft and deformable material. It may comprise a rather soft and/or deformable thermoplastic material or an elastomeric material, such like natural or synthetic rubber.

The impact absorbing structure can be sandwiched between the impact receiving structure and the reorientation member. However, the reorientation member may also provide and serve as an impact absorbing structure. Hence, the impact absorbing functionality may be embedded into the reorientation member.

Consequently and according to a further embodiment, the impact absorbing structure is integrated into the reorientation member and/or into the impact receiving structure. The impact receiving structure and/or reorientation member then fulfils a two-fold functionality. Additional to a reorientation or impact receiving function, the respective reorientation member and/or impact receiving structure also serves to absorb mechanical impact and serves to provide a dampening of the impact incident on the medical device and the medical device protection assembly.

In a further independent aspect, a portable medical device is provided, which comprises at least one medical device protection assembly as described above. Preferably, at least a selected end portion of the housing of the medical device is interconnected and/or covered by the medical device protection assembly.

However, also several housing portions of the medical device can be covered and/or surrounded by the medical device protection assembly. It is even conceivable, that the medical device protection assembly provides a shell completely surrounding the housing of the medical device. Then, the medical device protection assembly preferably comprises a non-homogeneous weight distribution and/or a reorientation member is positioned inside the housing of the medical device.

In another embodiment, the medical device comprises a drug delivery device in particular an injection device, such like a pen-type injector. Alternatively, the medical device may also comprise an analysis device, such like a blood glucose monitoring device.

Moreover and according to a further embodiment, the drug delivery device, in particular the injection device comprises at least one cartridge filled with a medicament to be administered or delivered to a patient.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25, Asp28] Exendin-4(1-39)-NH2,
H-Asn-(Glu)5-des Pro36, Pro37, Pro38 [Met(O)14, Trp(02)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments will be described by making reference to the drawings, in which.

DETAILED DESCRIPTION

Figure 1:
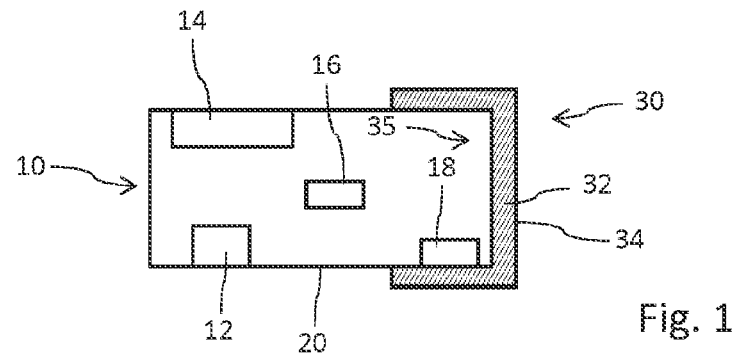
FIG. 1 schematically illustrates a medical device assembled with a medical device protection assembly according to a first embodiment, FIG. 2 schematically illustrates a second embodiment of a medical device protection assembly.

The medical device 10 as schematically illustrated in FIGS. 1 to 4 comprises a housing 20 and may be equipped with numeral device components 12, 14, 16, 18. The device component 12 may for instance provide a configuration and control means, such like control and operation buttons, knobs, dials or comparable operating elements. The device component 14 may comprise an input/output means, such like a display element, by way of which device specific information can be visually and/or audibly provided to a user.

Moreover, the device 10 may comprise a communication module 18, by way of which treatment- or analysis-related data can be stored and/or communicated and transferred to other devices, such like personal computers. Additionally, the medical device 10 may comprise a device component 16 which contains a medicament to be administered to a patient. In the event, that the medical device 10 is designed as a drug delivery device, the device component 16 may comprise a cartridge, such like a vitreous ampoule or carpule comprising a liquid medicament to be dispensed.

The various device components 12, 14, 16, 18 but also the housing 20 of the device 10 may be rather sensitive and susceptible with regard to mechanical impact. Therefore, a medical device protection assembly 30 is provided, which comprises a reorientation member 32 arranged at a pre-defined end section of the housing 20 of the medical device 10. As illustrated in FIG. 1 the reorientation member 32 is of u- or cupped shape and comprises a receptacle 35 to receive a right handed portion of the housing 20 of the medical device 10.

The reorientation member 32 provides an additional weight to the medical device 10 and serves to shift and to displace the centre of gravity of the medical device 10 towards the reorientation member 32. In the event, the medical device 10 may inadvertently drop down towards a surface, the reorientation member 32 serves to turn and to reorient the medical device 10 in such a way that the reorientation member faces toward the surface and that the reorientation member 32 impacts the respective surface first.

In this way, remotely located device components 12, 14, 16 can be effectively protected against mechanical impact. This applies to both, electronically implemented device components 12, 14 as well as two breakable device components, such like medicament-containing cartridges.

The reorientation member 32 may be releasably attached to the medical device 10. It may further comprise or may be at least partially covered with an impact receiving structure 34, which in the embodiment according to FIG. 1 provides an outer shell of the reorientation member 32. However, also an outer surface of the reorientation member 32 that faces away from the medical device 10 may serve as an impact receiving structure.

Additionally or alternatively the reorientation member 32 may comprise or provide an impact absorbing functionality such that mechanical impact incident on the reorientation member 32 can be at least partially absorbed and/or dissipated in a controlled way.

In the event of an incident mechanical impact, the reorientation member 32 and/or an impact receiving structure 34, 44, 54, 64 may become subject to a well-defined breakage, thereby indicating to a user, that the medical device protection assembly 30, 40, 50 has been shock-excited and that it should be replaced by an intact device protection assembly.

The various medical device protection assemblies 30, 40, 50, 60 as shown in FIGS. 1 to 4 may either be permanently or releasably engaged with the housing 20 of the medical device 10. With releasably connected medical device protection assemblies 30, 40, 50, 60 a broken protection assembly 30, 40, 50, 60 can be easily replaced by a new one. With particular medical devices 10, such a user-implementable replacement may be disadvantageous, since in the medical device 10 may have been invisibly damaged and may require inspection or repair. In such situations, it is beneficial when the medical device protection assembly 30, 40, 50, 60 is permanently and non-releasably connected with the housing 20 of the medical device 10, thus encouraging the end user to let the device inspect by a customer support.

Figure 2:
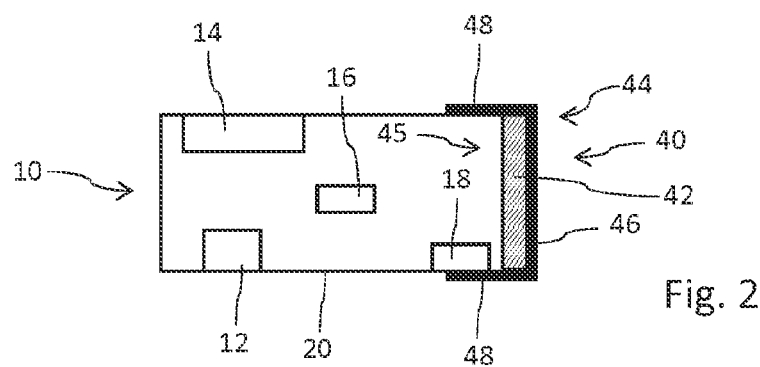

In the embodiment according to FIG. 2, the reorientation member 42 is arranged at an end face of the housing 20 of the medical device 10. Here, the reorientation member 42 also provides an additional reorientation inducing weight. Their reorientation member 42 may either be individually attached to the housing 20 or may be indirectly attached to the housing 20 by means of the impact receiving structure 44, which entirely covers the reorientation member 42.

As illustrated in FIG. 2, the impact receiving structure 44 comprises a u-shaped cross section and may comprise a cupped receptacle 45 having a bottom portion 46 and an adjacent side wall portion 48 by way of which a mutual engagement of housing 20 and impact receiving structure 44 can be established.

Here, it is also conceivable that the impact receiving structure 44 is operably connected to the housing 20 only via the reorientation member 42. Hence, the medical device protection assembly 40 may be preconfigured and may comprise the cup-shaped impact receiving structure 44 having the reorientation member 42 readily assembled therein. An interconnection of the medical device protection assembly 40 with the housing 20 of the medical device 10 could then also be provided by only fixing the reorientation member 42 to the respective end face of the housing 20 of the medical device 10.

Figure 3:
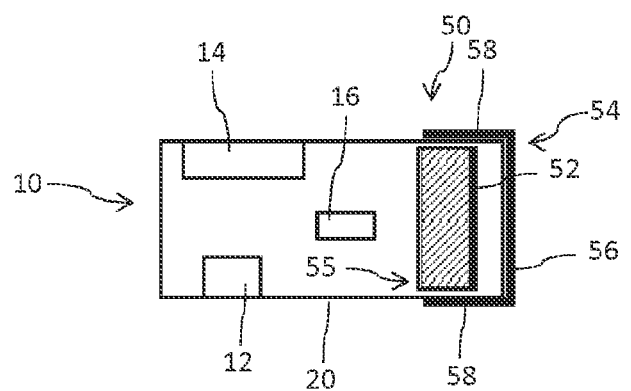
FIG. 3 shows another embodiment of a medical device protection assembly and FIG. 4 shows a further embodiment of a medical device protection assembly.

FIG. 3 is illustrating of another embodiment of a medical device protection assembly 50. Here, the protection assembly 50 comprises a cup-shaped impact receiving structure 54 comparable to the one as already illustrated and described with respect to FIG. 2. In contrast to the embodiment of FIG. 2, the reorientation member 52 is arranged inside the housing 20 of the medical device 10. In typical embodiments, the reorientation member 52 may even comprise a functional component of the medical device 10. It may for instance provide or serve as a battery.

Typically, the reorientation member 55 is positioned in a portion of the housing 20 which is at least partially covered by the impact receiving structure 54. Also here, the impact receiving structure 54 comprises a bottom portion 56 and a sidewall portion 58 to form a cup-shaped receptacle 55 adapted to receive a right-handed end section of the housing 20 of the drug delivery device 10.

Figure 4:
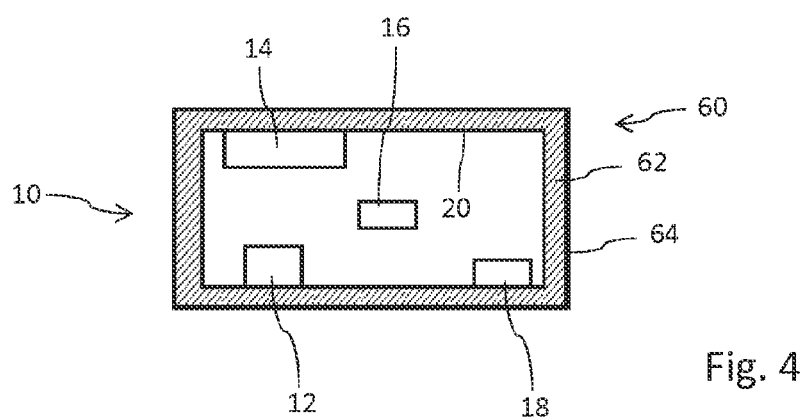

The embodiment according to FIG. 4 shows another implementation of a medical device protection assembly 60. Here, the reorientation member 62 entirely surrounds the housing 20 of the medical device 10. In order to provide a respective reorientation functionality, the reorientation member 62 then typically features a non-homogeneous weight distribution. Additionally, the reorientation member 62 may provide an impact absorbing structure, which in response to a mechanical impact above a certain threshold may deform, crack or even disintegrate. The reorientation member 62 may be further covered by an impact receiving structure 64 which may comprise a comparatively hard shell, which is able to withstand comparatively large mechanical impact.

The embodiment according to FIG. 4 may therefore comprise a kind of a second shell of the medical device, which in case of a damaging mechanical impact could be preferably replaced.

The invention claimed is:

1. A medical device protection assembly comprising:
at least one reorientation member being connectable to only an end portion of an outer surface of a housing of a medical device configured as a drug delivery device, the reorientation member when connected to the medical device being operable to orient the medical device into a predefined orientation in the event the medical device is subject to a free-fall, wherein the reorientation member comprises a cup-shaped receptacle configured to cover the end portion of the outer surface of the housing, where the reorientation member contains a reorientation weight such that when the reorientation member is attached to the housing, a center of gravity of the medical device is changed, wherein the reorientation member further comprises an impact receiving structure covering the reorientation member, where the impact receiving structure is not part of the housing of the medical device, and wherein an impact absorbing structure is integrated into the reorientation member or the impact receiving structure.

2. The medical device protection assembly, according to claim 1, wherein the impact receiving structure at least partially covers the reorientation member.

3. The medical device protection assembly according to claim 1, wherein the reorientation member is fixable to the housing of the medical device by means of the impact receiving structure.

4. The medical device protection assembly, according to claim 1, wherein the entire reorientation member is releasably engageable with the housing of the medical device.

5. The medical device protection assembly according to claim 1, wherein the impact receiving structure is mechanically reinforced.

6. A portable medical device comprising a protection assembly according to claim 1.

7. The medical device according to claim 6 further comprising an injection device or an analysis device.

8. The medical device according to claim 7 further comprising a cartridge being at least partially filled with a medicament.

9. A medical device protection assembly comprising:
at least one reorientation member arranged inside a housing of a medical device configured as a drug delivery device, the housing comprising a first end, a second end opposite to the first end, a front face, and a back face, wherein the front face and the back face extend between the first end and the second end, the front face and the back face each having a length larger than a length of the first end and the second end, wherein the at least one reorientation member is located inside either the first end or the second end, and wherein the reorientation member is operable to orient the medical device into a predefined orientation in the event the medical device is subject to a free-fall, where the reorientation member contains a reorientation weight configured to modify a center of gravity of the medical device to be located at the first end or the second end; and
an impact receiving structure covering the one of the first end or the second end of the housing that is provided with the reorientation weight, where the impact receiving structure is not part of the housing of the medical device.

10. The medical device protection assembly according to claim 9, wherein the reorientation member comprises a battery.

11. The medical device protection assembly of claim 9 where the impact receiving structure comprises a cup-shaped receptacle configured to cover a portion of an outer surface of the first end or the second end of the housing.

12. A medical device protection assembly comprising:
at least one reorientation member being connectable to a housing of a medical device, the housing comprising a first end, a second end opposite to the first end, a front face, and a back face, wherein the front face and the back face extend between the first end and the second end, wherein the at least one reorientation member is configured to cover the first end, the second end, the front face, and the back face of the housing and the at least one reorientation member is operable to orient the medical device into a predefined orientation in the event the medical device is subject to a free-fall, wherein the reorientation member comprises a weight that is non-homogeneously distributed within the reorientation member such that when the reorientation member is attached to the housing, a center of gravity of the medical device is changed, and wherein the reorientation member further comprises an impact receiving structure covering the reorientation member, where the impact receiving structure is not part of the housing of the medical device.

13. A medical device protection assembly comprising:
a cup-shaped body comprising a receptacle configured to receive a housing of a medical device, the medical device being a pen-type injector, wherein the housing comprises a first end, a second end, and a cylindrical portion extending between the first end and the second end, wherein the cup-shaped body is configured to receive only either the first end or the second end; and
a reorientation member located in the cup-shaped body and being operable to orient the medical device into a predefined orientation when the cup-shaped body is attached to one of the first end or the second end in the event the medical device is subject to a free-fall, wherein the reorientation member comprises a reorientation weight such that when the cup-shaped body is attached to the housing, a center of gravity of the medical device is changed, and wherein the cup-shaped body further comprises an impact receiving structure covering the cup-shaped body, where the impact receiving structure is not part of the housing of the medical device.

* * * * *